US00RE36473E

United States Patent [19]

Esch et al.

[11] E Patent Number: Re. 36,473

[45] Reissued Date of Patent: Dec. 28, 1999

[54] FIBEROPTIC DELIVERY SYSTEM AND METHOD OF USE

[75] Inventors: Victor C. Esch, San Francisco; Kirsten L. Valley, Mountain View, both of Calif.

[73] Assignee: Indigo Medical, Inc., Palo Alto, Calif.

[21] Appl. No.: 08/976,528

[22] Filed: Nov. 21, 1997

Related U.S. Patent Documents

Reissue of:

[64] Patent No.: 5,469,524
Issued: Nov. 21, 1995
Appl. No.: 08/241,735
Filed: May 12, 1994

[51] Int. Cl.[6] ..... G02B 6/06

[52] U.S. Cl. ..... 385/118; 385/117; 606/7; 606/15

[58] Field of Search ..... 385/115, 116, 385/117, 118, 119, 120, 901; 606/7, 12, 15, 4, 16, 9, 17, 10

[56] References Cited

U.S. PATENT DOCUMENTS 4,564,011 1/1986 Goldman .
4,865,029 9/1989 Pankratov et al. ..... 606/4
4,950,267 8/1990 Ishihara et al. .
5,207,672 5/1993 Roth et al. .
5,222,174 6/1993 Miles ..... 385/118
5,239,982 8/1993 Trauthen ..... 606/117
5,301,658 4/1994 Zhu et al. ..... 606/191 X

FOREIGN PATENT DOCUMENTS 2-121675 5/1990 Japan .
92/10142 6/1992 WIPO .

*Primary Examiner*—Phan T. H. Palmer
*Attorney, Agent, or Firm*—Bernard Shay

[57] ABSTRACT

A hand held device having an optical fiber with a radiation emitter carried at a free end, the optical fiber being attached to a handle that includes a knob which allows movement of a flexible tubular sleeve from a position covering the fiber and emitter to a position exposing the emitter and a length of fiber adjacent to it, the sleeve also having a sharp metal cleat extending from its end, the cleat being an end of a length of wire which passes through a separate channel of the sleeve to the knob without being attached to the sleeve. An application of this device is for inserting the emitter into a mass of material in order to irradiate the material from within.

74 Claims, 3 Drawing Sheets

FIBEROPTIC DELIVERY SYSTEM AND METHOD OF USE

Matter enclosed in heavy brackets [ ] appears in the original patent but forms no part of this reissue specification; matter printed in italics indicates the additions made by reissue.

BACKGROUND OF THE INVENTION

This invention relates to devices used with optical fibers to assist in inserting optical fiber ends into a mass of material to be irradiated through the fiber.

Therefore, it is a primary object of the present invention to provide a hand-held device with improved ease of use to assist insertion of an optical fiber end into a volume of material to be irradiated.

It is another object of the present invention to provide a more precise method, utilizing such a device, of implanting an end of an optical fiber in such a volume of material.

SUMMARY OF THE INVENTION

According to a primary aspect of the present invention, briefly and generally, a hand held device, from which an optical fiber extends with an end carrying a radiation emitter, is provided with a retractable sleeve normally surrounding the extended fiber and emitter, and a hand operated knob to allow retraction of the sleeve into a body of the device. A free end of the sleeve is cut at an angle to form a point to assist piercing a surface of a mass of material into which the fiber is implanted. The sleeve is made of flexible material, preferably a plastic, in order to allow its insertion through a curved passage of a device that assists guiding the sleeve and its internal flexible optical fiber into position for piercing the material surface.

Flexible plastic material suitable for the sleeve will likely lack the degree of rigidity necessary for its sharp point to adequately pierce through the material surface at a desired location without first buckling and then sliding along the outside surface of the surface to another location. Thus, a small diameter wire is carried within the sleeve to extend a short distance out of its end to form a cleat that assists in piercing the material surface at the location where the user first positions the sleeve tip. This wire is preferably contained in a separate passage within the sleeve but is not attached to it. Rather, an end of the wire, opposite to that of the cleat, is attached to the knob, thereby causing the wire to move back and forth with respect to the body simultaneously with the sleeve. This assures that the extended cleat will not be dislodged in the material and also results in the cleat being extended an additional distance from the sleeve tip when the sleeve and fiber are bent during insertion into a curved channel of an instrument with which the improved device of the present invention may be utilized. A measurement scale is printed on an outside surface of the sleeve in order to provide an easy indication of the distance in which the optical fiber is inserted into the body of material. Once inserted to a desired depth, the sleeve is withdrawn by moving the knob with respect to the body of the device, leaving the optical fiber and emitter within the body of material. Radiation may then be applied to the emitter through the optical fiber.

Additional objects, advantages and features of the present invention will become apparent from the following description of its preferred embodiments, which description should be taken in conjunction with the accompanying drawings.

DESCRIPTION OF A PREFERRED EMBODIMENT

Figure 1:
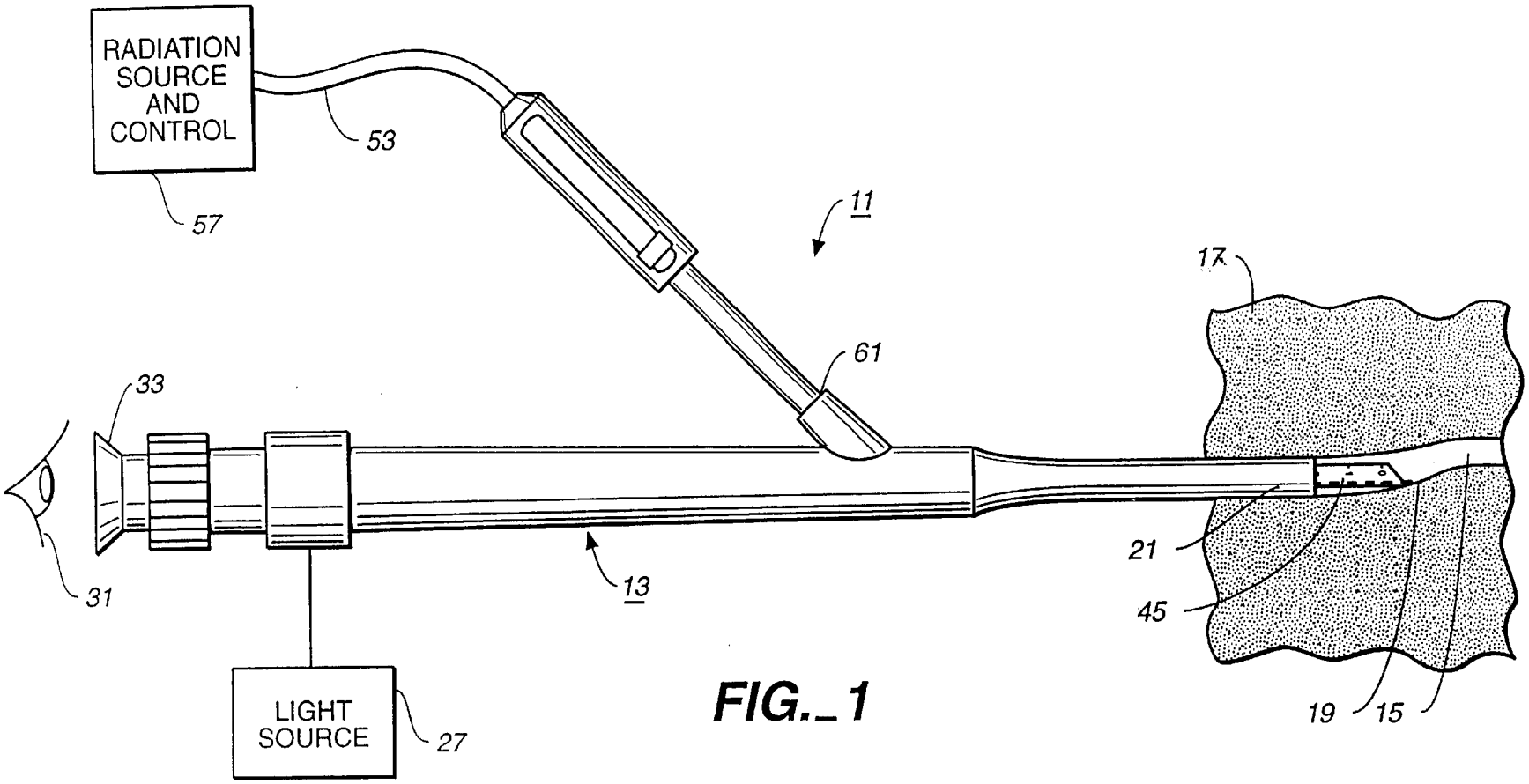
FIG. 1 illustrates a use of the improved fiberoptic delivery system according to the present invention, utilizing an auxiliary instrument to position it.

Although the fiberoptic delivery system according to the present invention can be used to implant an end of an optical fiber into a wide variety of types of solid or semi-solid materials, an application illustrative with respect to FIG. 1 is for insertion of the optical fiber end into biological tissue of a human or other body. With reference to FIG. 1, a device 11 according to the present invention is used with an endoscope 13 of a type commonly used by physicians for working inside a passage or cavity of a patient. Such a passage 15 is generically illustrated in FIG. 1 to pass through a volume of tissue material 17 with a wall formed by a tissue surface 19. As an example, the tissue 17 can be a male prostate and the passage 15 can be his urethra or rectum. One very specific application of the improved fiberoptic delivery system of the present invention is to treat benign prostate hyperplasia (BPH) of men. An optical fiber emitter is inserted into one or more lobes of the prostate to heat a volume therein by application of electromagnetic radiation within the infra-red range of the spectrum.

Figure 2:
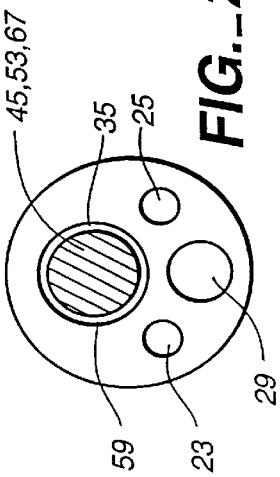
FIG. 2 is a view of the right hand end of the auxiliary instrument of FIG. 1.

A view of an end 21 of a typical endoscope 13 of FIG. 1 is shown in FIG. 2. When this end is inserted within a body passage, that passage is illuminated by light emitted from the ends 23 and 25 of optical fibers that are connected to an external light source 27. A lens 29 and other optics within the body of the endoscope 13 allow a user 31 to view the internal passage through an eye-piece 33. A channel 35 that is provided in the endoscope 13 for introduction of fluids or some other instrument into the passage is utilized to guide and position the improved delivery system 11 of the present invention.

Figure 3:
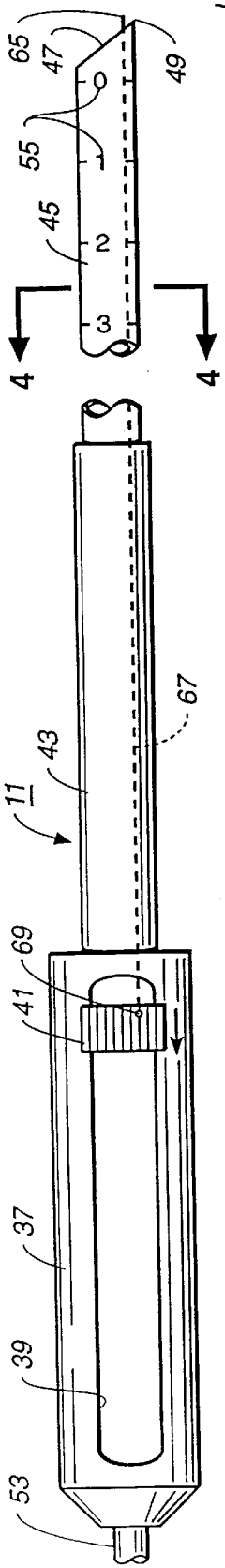
FIG. 3 illustrates an embodiment of the improved fiberoptic delivery system according to the present invention.

Referring to FIG. 3, the major components of the delivery system 11 will now be explained. A main body includes a handle 37 having a slot 39 in which a knob 41 is slidable back and forth. Fixed to this semi-rigid handle 37 is a semi-rigid, hollow tubular shaft 43. A flexible plastic sleeve 45 is carried within an opening of the shaft 43 in a manner to be slidable back and forth within the shaft 43. The sleeve 45 has a free end 47 cut at an angle to create a point 49 to assist in piercing the surface of material in which an emitter 51 (FIG. 5) at an end of an optical fiber 53 is to be inserted. An opposite end of the sleeve 45 is connected to the knob 41 so as to be moveable back and forth with respect to the handle 37 and shaft 43 as the knob 41 is moved. FIG. 3 shows the sleeve 45 being fully extended away from the shaft 43, while FIG. 5 shows the opposite, namely the sleeve 45 being withdrawn a maximum amount within the handle 37 and shaft 43 by movement of the knob 41 to an opposite end of the slot 39.

Figure 5:
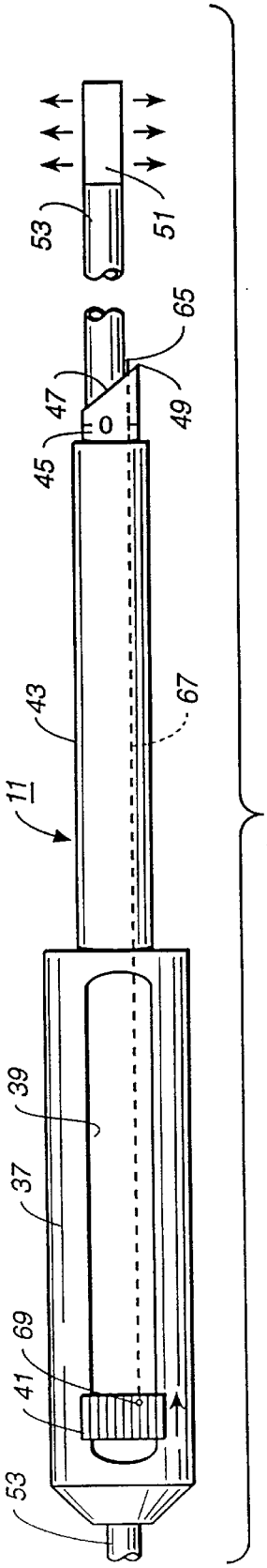
FIG. 5 is a view of the fiberoptic delivery system of FIG. 3 with a sleeve thereof having been repositioned.

The optical fiber 53 is fixedly attached to the handle 37 so that withdrawal of the sleeve 45 into the position shown in FIG. 5 leaves the optical fiber 53 and its radiation emitter 51 fully extended from the shaft 43. The radiation emitter 51, for the applications contemplated, will generally be a diffusing tip that emits radiation with substantially the same intensity along the length and around its outer cylindrical surface. However, the improved fiberoptic delivery system according to the present invention can be used with any type of emitter as is appropriate for the specific application, including use of a bare fiber end without any special emitter attached to it.

The tip 49 of the sleeve 45 is used to pierce a surface of the material into which the optical fiber is to be inserted. A sleeve 45 and the optical fiber 53 are inserted through the surface into the material without any relative movement between the fiber 53 or sleeve 45. This manipulation is done by hand by gripping the handle 37. A sleeve 45 and its fiber 53 are then pushed into the material a desired distance as indicated by a scale 55 printed on an outside surface of the sleeve 45. This scale, as shown, has a "0" marking coincident with the position of an exposed end of the emitter 51. The scale 55 then measures back from that endpoint in some convenient unit, such as inches or centimeters. Once the sleeve is inserted into the body of material with the outer surface at the desired depth marking of the scale 55, the knob 41 is then slid from the position shown in FIG. 3 to that shown in FIG. 5 in order to remove the sleeve 45 from the material altogether or at least well out of the way of the emitter 51. Electromagnetic radiation is then applied through the optical fiber 53 from a diode laser or other appropriate source within an instrument 57 (FIG. 1). When the treatment is completed, the fiber is removed from the material by gripping the handle 37 and removing the entire device 11 back away from the material.

Figure 6:
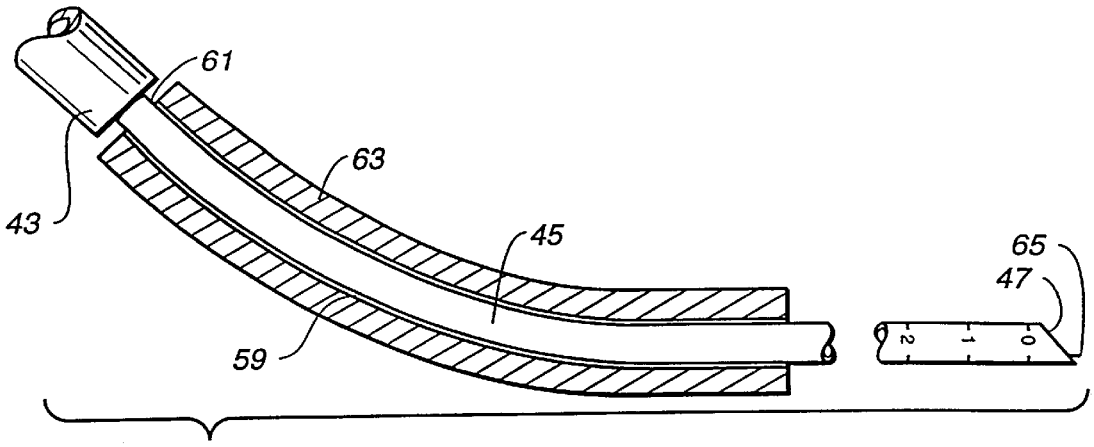
FIG. 6 illustrates use of the improved fiberoptic delivery system of FIGS. 3–5 within a curved passage of the auxiliary instrument shown in FIG. 1.

The sleeve 45 is made of a flexible material so that it can be inserted into a curved instrument channel 59 of a typical endoscope 13 or other instrument used in conjunction with the device of the present invention. The end 49 of the sleeve 45 is inserted into a port 61 (FIGS. 1 and 6) at an end of the channel 59, and then urged down along the channel to emerge out of its end illustrated in FIG. 2. Since available optical fibers inserted into the sleeve 45 are also flexible, the combination may follow the curved path of the instrument channel 59. The channel 59 is usually formed to have a circular cross-section with metal walls of a rigid piece 63.

In order to provide the sleeve 45 with this flexibility, the plastic material that is chosen for it is necessarily relatively soft, certainly much softer than would be a rigid metal sleeve. Therefore, the point 49 of the sleeve 45 will not usually be an effective cutting tool to pierce the surface of the material into which the sleeve 45 is to be inserted. Especially when the sleeve is oriented at a small angle with respect to the outer material surface, a sharp piercing point is important. When so oriented at a small acute angle with respect to the surface to be pierced, the tip 49 typically moves around the surface from the position where the user intends to penetrate the material surface to some other position removed from it. Therefore, in order to provide for sure penetration at the location where the user first positions the sleeve point 49, a metal cleat 65 is extended a short distance from the free end of the sleeve 45 adjacent to its point 49. The cleat 65 thus immediately penetrates the surface of the material when the user pushes the end 47 against the surface, even when held at a small acute angle with respect thereto.

Figure 4:
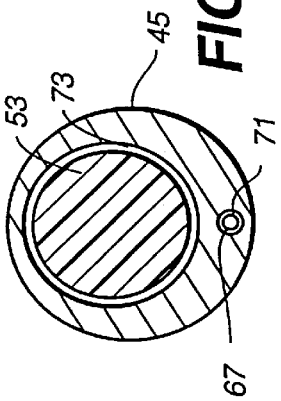
FIG. 4 is a sectional view of the system of FIG. 3, taken at section 4—4 thereof.

Rather than simply affixing a short metal piercing element to the end 47 of the sleeve 45, however, the cleat 65 is formed at the end of a length of stainless steel wire 67 that passes through the sleeve 45 without attachment to it. The wire 67 is instead attached at an opposite end 69 thereof to the knob 41. The wire 67 has a small, uniform cross-section along its length and may tend to bend when pushed at its cleat end. In order to prevent such bending, the wire 67 is constrained in a channel 71 (FIG. 4) of the sleeve 43 that has a uniform circular cross-section only slightly larger than that of the wire 67. As an example, the wire 67 may be less than one millimeter in diameter, preferably about 0.2 millimeter, and the passage 71 less than two millimeters in diameter, preferably about 0.3 millimeter. A secondary purpose of the wire is to increase the sleeve's rigidity, which is desirable for transmitting surface piercing force and adding resistance to buckling. The optical fiber 51 is carried in a separate passage 73 within the sleeve 45.

By being attached at the end 69 to the knob 41, the wire 67 will move back and forth with respect to the shaft 43 in the same manner as the sleeve 45 when the knob 41 is operated within the handle slot 39. The avoidance of attachment of the wire 67 or cleat 65 to the sleeve 45 has certain advantages. One advantage is the reduction of a probability that the cleat 65 will be left behind in the volume of material after the sleeve 45 is withdrawn from it. A small piece of wire attached to the end 47 of the sleeve could suffer from that disadvantage, particularly undesirable if the material is biological tissue. But another advantage is that the cleat 65 may be made shorter than desirable for effective penetration of the material surface when used in the curved instrument channel 59 (FIG. 6) of a typical endoscope instrument 13. That is because the curvature of the sleeve 45 in that channel causes the wire 67 to protrude further from the sleeve end 47 than when the sleeve is straight. Thus, the cleat 45 can be made to be short enough so that it does not scrape along the interior wall of the instrument channel 61 as it is being inserted therethrough but still is long enough when used to pierce a surface of the material into which the optical fiber emitter 51 is to be implanted for internal radiation thereof.

Figure 7A:
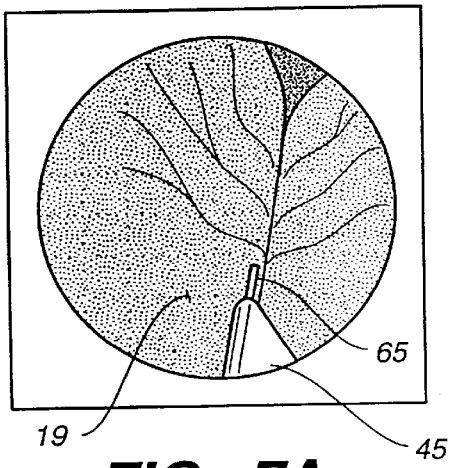
FIGS. 7A, 7B and 7C represent views through the auxiliary instrument of FIG. 1 that shows different stages in the insertion therethrough of the improved fiberoptic delivery system of FIGS. 3–5.
Figure 7B:
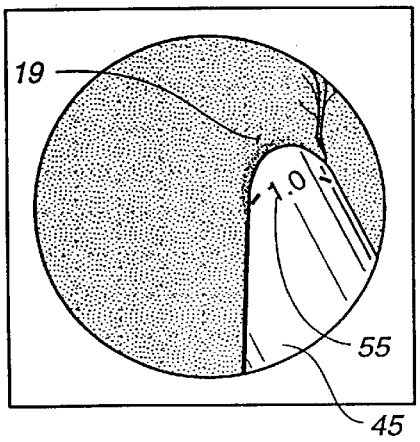
Figure 7C:
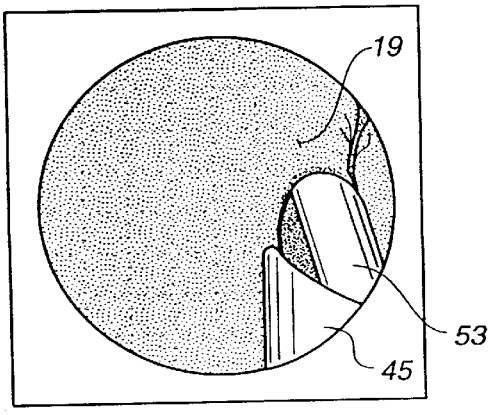

FIGS. 7A, 7B and 7C show three views of the user 31 through the eyepiece 33, lens 29 and other optics of the endoscope 13, when the optical fiber emitter is being inserted in biological tissue generally in a manner illustrated in FIG. 1. Once the end 21 of the endoscope 13 is positioned within the passage 15 so that user 31 can view the region of the surface 19 through which the fiber emitter is to be implanted, the device 11 of the present invention is manipulated to insert into the channel port 61 and through the instrument channel 59 the optical fiber 53 with the sleeve 45 extended to cover it, in the position shown in FIG. 3. The sleeve 45 and fiber 51 are urged through that endoscope channel until the user sees it within the field of view, the position shown in FIG. 7A. A endoscope 13 is then tilted (not shown) with respect to the passage 15 in order to increase the angle of incidence of the sleeve 45 with the surface 19 to be pierced. The sleeve 45 is then pushed further through the instrument channel 59 of the endoscope 13 to pierce the surface 19. The sleeve 45 and fiber within it are then urged further until the appropriate marking on the scale 55 appears adjacent the surface 19 being pierced. Such a view is shown in FIG. 7B. After inserted to the desired depth, the knob 41 of the device 11 is then moved backwards, from the position shown in FIG. 3 to that shown in FIG. 5, to remove the sleeve from within the material. FIG. 7C shows the sleeve 45 being removed from within the volume of material leaving the optical fiber 53 emersed therein. After the step illustrated in FIG. 7C, the radiation source of the instrument 57 (FIG. 1) is energized for a time to provide the desired radiation through the emitter 51 to the interior portion of the volume.

Although the various aspects of the present invention have been described with respect to the preferred embodiment thereof, it will be understood that the invention is entitled to protection within the full scope of the appended claims.

It is claimed:

1. A hand held fiber optic delivery system, comprising:

a handle, a flexible elongated tube carried by the handle in a manner to be slid in and out thereof for a distance along the length of the tube, said tube having a free end extending a distance from the handle, a knob carried by the handle and attached to said tube therein in a manner to allow said tube to be slid in and out of the handle along the length of the tube, a length of optical fiber positioned within said tube and handle, said optical fiber being restrained against movement along its length by attachment to the handle, and a length of wire extending along the length of said tube, said wire being attached to said knob and extending a distance away from said free tube end, whereby said wire and tube are moved together along their lengths by movement of the knob with respect to the handle.

2. The system of claim 1 wherein said wire is of an uniform diameter along its length within the tube and remains unattached to said tube, thereby allowing the wire to slide along its length with respect to the tube when the tube is bent.

3. The system of claim 2 wherein the tube includes a first passage extending along its length in which the optical fiber is carried and a second passage extending parallel to said first passage in which the wire is carried, said second passage having a diameter no more than twice that of said wire.

4. The system of claim 3 wherein the tube is made of a plastic material and the wire is made of a metallic material.

5. The system of claim 1 which additionally comprises measurement marks periodically spaced apart on an outside of the tube along its length adjacent said free end with indicia of a distance of the marks from said free end of the tube.

6. A method of inserting an end of an optical fiber into biological tissue through a passage of a body, comprising the steps of:

inserting an endoscope into said passage and positioning a far end thereof adjacent a surface of the tissue into which the optical fiber end is desired to be inserted, feeding through the endoscope an end of a flexible tube containing an optical fiber by manipulation of a handle to which the tube and fiber are attached, piercing the surface of the tissue by first urging thereinto a tip of a wire that extends along the length of the tube end and beyond its said one end, inserting the tube and optical fiber a desired distance within the tissue as determined by observing measurement markings along a length of the tube on its outside surface, and thereafter withdrawing the tube from the tissue while holding the optical fiber against such withdrawal, whereby the optical fiber end is positioned within the tissue for treatment thereof.

7. A hand held fiber optic delivery system, comprising:

a handle, a flexible elongated tube carried by the handle in a manner to be slid in and out thereof for a distance along the length of the tube, said tube having a free end extending a distance from the handle, a knob carried by the handle and attached to said tube therein in a manner to allow said tube to be slid in and out of the handle along the length of the tube, a length of optical fiber positioned within said tube and handle, said optical fiber being restrained against movement along its length by a attachment to the handle, a length of wire extending along the length of said tube, said wire being attached to said knob and extending a distance away from said free tube end, whereby said wire and tube are moved together along their lengths by movement of the knob with respect to the handle, and measurement marks periodically spaced apart on an outside of the tube along its length adjacent said free end with indicia of a distance of the marks from said free end of the tube.

8. The system of claim 7 wherein said wire is of a uniform diameter along its length within the tube and remains unattached to said tube, thereby allowing the wire to slide along its length with respect to the tube when the tube is bent.

9. The system of claim 8 wherein the tube includes a first passage extending along its length in which the optical fiber is carried and a second passage extending parallel to said first passage in which the wire is carried, said second passage having a diameter no more than twice that of said wire.

10. The system of claim 9 wherein the tube is made of a plastic material and the wire is made of a metallic material.

*11. A method of inserting a radiation emitting end of an optical fiber system into biological tissue through a passage of a body, comprising:*

*inserting an endoscope into the passage and positioning a far end thereof adjacent a surface of the tissue into which the radiation emitting end is desired to be inserted;*

*feeding the radiation emitting end through the endoscope by manipulation of the optical fiber system;*

*piercing the surface of the tissue using a tip of the optical fiber system and urging the radiation emitting end of the optical fiber system into the tissue;*

*positioning the radiation emitting end a desired distance within the tissue as determined by observing a measurement marking along a length of the optical fiber system on an outside surface thereof, whereby the radiation emitting end is positioned within the tissue; and*

*energizing a radiation source connected to the optical fiber system to provide radiation through the radiation emitting end to the tissue.*

*12. The method according to claim 11 wherein the optical fiber system further comprises an optical fiber and a flexible sleeve surrounding at least a portion of the optical fiber.*

*13. The method according to claim 12 wherein the radiation emitting end of the optical fiber system comprises a diffusing tip.*

*14. The method according to claim 13 wherein the diffusing tip is substantially cylindrical and is adapted to emit radiation with a substantially uniform intensity alone a length thereof and around an outer cylindrical surface thereof.*

*15. The method according to claim 14 wherein the radiation source comprises a diode laser.*

*16. The method according to claim 13 wherein the radiation source comprises a diode laser.*

*17. The method according to claim 12 wherein the optical fiber system includes a sharp piercing point.*

*18. The method according to claim 17 wherein the endoscope is tilted with respect to the passage prior to piercing the surface of the tissue to increase an angle of incidence of the sleeve with respect to the surface of the tissue.*

*19. The method according to claim 12 wherein said sleeve is urged into the tissue until a selected measurement marking is positioned adjacent the surface of the tissue.*

*20. A method of inserting a diffusing tip, which is positioned at an end of an optical fiber, into a prostate gland through a urethra for the purpose of treating benign prostate hyperplasia, comprising:*

*inserting an endoscope into the urethra and positioning a far end thereof adjacent a surface of the prostate gland;*

*feeding the diffusing tip through the endoscope by manipulation of the optical fiber;*

*piercing the surface of the prostate gland and urging the diffusing tip into the prostate gland;*

*positioning the optical fiber and the diffusing tip a desired distance within the prostate gland as determined by observing a measurement marking along an outer surface of a length of a flexible sleeve positioned around at least a portion of the optical fiber, whereby the diffusing tip is positioned within the prostate gland; and*

*energizing a radiation source connected to the optical fiber to provide radiation through the diffusing tip to tissue of the prostate gland.*

*21. The method according to claim 20 wherein the diffusing tip is substantially cylindrical and is adapted to emit radiation with a substantially uniform intensity alone a length thereof and around an outer cylindrical surface thereof.*

*22. The method according to claim 21 wherein the radiation source comprises a diode laser.*

*23. The method according to claim 20 wherein the endoscope is tilted with respect to the urethra prior to piercing the prostate gland to increase an angle of incidence of the sleeve with respect to the surface of the prostate gland.*

*24. The method according to claim 20 wherein the sleeve is urged into the tissue of the prostate gland until a selected measurement marking is positioned adjacent the surface of the prostate gland.*

*25. The method according to claim 20 wherein the optical fiber and the sleeve are affixed to each other to prevent significant relative movement therebetween.*

*26. A method of inserting an end of an optical fiber into tissue of the prostate gland through a urethral passage of a human body for the purpose of treating benign prostate hyperplasia, comprising:*

*inserting an endoscope into the passage and positioning a far end thereof adjacent a surface of the tissue into which the optical fiber end is desired to be inserted;*

*feeding a sleeve through the endoscope by manipulation of the sleeve wherein at least a portion the optical fiber is enclosed in the sleeve;*

*piercing the surface of the tissue by urging thereinto a tip of the sleeve, wherein the tip extends beyond the optical fiber end;*

*positioning the sleeve and the optical fiber a desired distance within the tissue as determined by observing a measurement marking along a length of the sleeve on an outside surface thereof, whereby the optical fiber end is positioned within the tissue; and*

*energizing a radiation source connected to the optical fiber to provide radiation through the optical fiber to the tissue.*

*27. The method according to claim 26 wherein the radiation is emitted from the optical fiber end in a substantially cylindrical pattern therearound and with a substantially uniform intensity along a length thereof.*

*28. The method according to claim 27 wherein the radiation source comprises a diode laser.*

*29. The method according to claim 26 wherein the sleeve includes a sharp piercing point.*

*30. The method according to claim 29 wherein the endoscope is tilted with respect to the passage prior to piercing the surface of the tissue to increase an angle of incidence of the sleeve with respect to the surface of the tissue.*

*31. The method according to claim 26 wherein the radiation source comprises a diode laser.*

*32. The method according to claim 26 wherein the sleeve is urged into the tissue until a selected measurement marking is positioned adjacent the surface of the tissue being pierced.*

*33. The method according to claim 26 wherein the sleeve is flexible and the optical fiber is affixed to the sleeve to prevent relative movement between the sleeve and the optical fiber.*

*34. A hand-held, fiber optic delivery system for use with an endoscope, comprising:*

*a flexible elongated plastic sleeve adapted to be carried by the endoscope in a manner to be slid in and out of the endoscope and having a free end extending a distance from the endoscope;*

*a length of optical fiber positioned within said sleeve; and*

*measurement marks periodically spaced apart on an outside surface of said sleeve along the free end thereof.*

*35. The system according to claim 34, further comprising a radiation emitter at a distal end of said optical fiber.*

*36. The system according to claim 35 wherein said radiation emitter comprises a diffusing tip.*

*37. The system according to claim 36 wherein said diffusing tip emits radiation with a substantially uniform intensity along a length thereof and around an outer cylindrical surface thereof.*

*38. The system according to claim 34, further comprising a radiation source connected to said optical fiber.*

*39. The system according to claim 38 wherein said radiation source is a diode laser.*

*40. The system according to claim 34 wherein said measurement marks are indicative of a distance therefrom to the free end of said sleeve.*

*41. The system according to claim 34 wherein said optical fiber is affixed to said sleeve to prevent relative movement therebetween.*

*42. A hand-held, fiber optic delivery system for use with an endoscope, comprising:*

*a flexible elongated plastic sleeve adapted to be carried by the endoscope in a manner to be slid in and out of the endoscope and having a free end extending a distance from the endoscope;*

*a length of optical fiber positioned within said sleeve; and*

*means observable on said sleeve for indicating a distance between said means and the free end of said sleeve.*

*43. The system according to claim 42, further comprising a radiation source connected to said optical fiber.*

*44. The system according to claim 43 wherein said radiation source is a diode laser.*

*45. The system according to claim 42, further comprising means, at a distal end of said optical fiber, for emitting radiation with a substantially uniform intensity along a length thereof and around an outer cylindrical surface thereof.*

*46. The system according to claim 42 wherein said optical fiber is affixed to said sleeve to prevent relative movement therebetween.*

*47. A hand-held, fiber optic delivery system for inserting an optical fiber into biological tissue, comprising:*

*an optical fiber;*

*an endoscope;*

*a flexible elongated tube covering at least a portion of said optical fiber, said tube having a distal end and being positioned in said endoscope such that the distal end of said tube may be slid in and out of said endoscope; and*

*measurement marks periodically spaced apart on an outside of said tube along a length thereof adjacent the distal end.*

*48. The system according to claim 47, further comprising a radiation emitter at a distal end of said optical fiber.*

*49. The system according to claim 48 wherein said radiation emitter comprises a diffusing tip.*

*50. The system according to claim 49 wherein said diffusing tip emits radiation with a substantially uniform intensity along a length thereof and around an outer cylindrical surface thereof.*

*51. The system according to claim 47, further comprising a radiation source connected to said optical fiber.*

*52. The system according to claim 51 wherein said radiation source is a diode laser.*

*53. The system according to claim 47 wherein said measurement marks are indicative of a distance therefrom to the distal end of said tube.*

*54. The system according to claim 47 wherein said optical fiber is affixed to said tube to prevent relative movement therebetween.*

*55. A hand-held, fiber optic delivery system for inserting an optical fiber into biological tissue, comprising:*

*an optical fiber;*

*an endoscope;*

*a flexible elongated tube covering at least a portion of said optical fiber, said tube having a distal end and being positioned in said endoscope such that the distal end of said tube may be slid in and out of said endoscope; and*

*means observable on an outside of said tube along a length thereof adjacent the distal end for indicating a distance between said means and the distal end.*

*56. The system according to claim 55, further comprising a radiation source connected to said optical fiber.*

*57. The system according to claim 56 wherein said radiation source is a diode laser.*

*58. The system according to claim 55, further comprising means, at a distal end of said optical fiber, for emitting radiation with a substantially uniform intensity alone a length thereof and around an outer cylindrical surface thereof.*

*59. The system according to claim 55 wherein said optical fiber is affixed to said tube to prevent relative movement therebetween.*

*60. An optical fiber delivery system adapted to irradiate tissue of the prostate gland, comprising:*

*an optical fiber;*

*a flexible outer sleeve of plastic surrounding at least a portion of said optical fiber;*

*a radiation emitter located at a distal end of said optical fiber, said radiation emitter comprising a diffusing tip which emits radiation with a substantially uniform along a length thereof and around an outer cylindrical surface thereof;*

*a measurement scale along an outer surface of said sleeve, said scale including marks indicating a distance therefrom to an end of said flexible outer sleeve; and*

*an electromagnetic radiation source connected to said optical fiber to supply electromagnetic radiation to said radiation emitter, said electromagnetic radiation source comprising a diode laser.*

*61. The system according to claim 60, further comprising an endoscope, said optical fiber and said flexible outer sleeve being positioned to move within a channel of said endoscope.*

*62. The system according to claim 60 wherein said optical fiber is affixed to said sleeve to prevent relative movement therebetween.*

*63. An optical fiber delivery system adapted to irradiate tissue of the prostate gland, comprising:*

*an optical fiber;*

*a flexible outer sleeve of plastic surrounding at least a portion of said optical fiber;*

*a means at a distal end of said optical fiber for emitting radiation with a substantially uniform intensity along a length thereof and around an outer cylindrical surface thereof;*

*means along an outer surface of said sleeve for indicating a distance therefrom to an end of said flexible outer sleeve; and*

*means connected to said optical fiber for supplying electromagnetic radiation to said radiation emitting means.*

*64. The system according to claim 63 wherein said supplying means is a diode laser.*

*65. The system according to claim 63 wherein said optical fiber is affixed to said sleeve to prevent relative movement therebetween.*

*66. An optical fiber delivery system for use with an endoscope disposed within a passage of a body for access to biological tissue, comprising:*

*an optical fiber having a radiation emitting end at a distal end thereof;*

*a sleeve of sufficient flexibility for insertion into a channel of the endoscope, said sleeve surrounding at least a portion of said optical fiber;*

*means at a distal end of said sleeve for piercing a surface of the tissue;*

*means surrounding at least a portion of said sleeve for urging the radiation emitting end and said sleeve together into the tissue a desired distance; and*

*means observable on said sleeve for indicating the desired distance.*

*67. The system according to claim 66 wherein the radiation emitting end of said optical fiber comprises a diffusing tip.*

*68. The system according to claim 67 wherein the diffusing tip is substantially cylindrical and is adapted to emit radiation with a substantially uniform intensity along a length thereof and around an outer cylindrical surface thereof.*

*69. The system according to claim 66 wherein said piercing means includes a sharp piercing point.*

*70. The system according to claim 69 wherein, when the endoscope is tilted with respect to the passage, an angle of incidence between said sleeve and the surface of the tissue is sufficient for piercing the surface with the piercing point.*

*71. The system according to claim 66, further comprising a radiation source operably connected to a proximal end of said optical fiber.*

*72. The system according to claim 71 wherein said radiation source is a diode laser.*

*73. The system according to claim 66 wherein said indicating means includes a measurement marking on said sleeve.*

*74. The system according to claim 66 wherein said optical fiber is affixed to said sleeve to prevent relative movement therebetween.*

* * * * *